United States Patent [19]

Backhaus et al.

[11] Patent Number: 5,605,838
[45] Date of Patent: Feb. 25, 1997

[54] METHOD FOR THE QUANTITATIVE ANALYSIS OF SAMPLE LIQUID

[75] Inventors: Juergen Backhaus, Edingen-Neckarhausen; Reinhold Mischler, Ludwigshafen, both of Germany

[73] Assignee: Boehringer Mannheim GmbH, Mannheim, Germany

[21] Appl. No.: 307,415

[22] Filed: Sep. 19, 1994

[30] Foreign Application Priority Data

Sep. 17, 1993 [DE] Germany .................. 43 31 596.8

[51] Int. Cl.[6] ............................................ G01N 21/00
[52] U.S. Cl. .................. 436/34; 436/46; 436/87; 436/164; 436/165; 436/169; 436/170; 436/171; 436/177; 250/339.11; 250/339.12; 356/36; 356/445; 356/446
[58] Field of Search ............................. 436/46, 87, 164, 436/169, 165, 170, 171, 177, 34; 250/339.11, 339.12; 356/36, 445, 446

[56] References Cited

U.S. PATENT DOCUMENTS

| | | |
|---|---|---|
| 3,748,909 | 7/1973 | Kuo .......................... 73/425.4 |
| 3,768,978 | 10/1973 | Grubb et al. ............... 23/239 |
| 3,898,982 | 8/1975 | Katsuda ..................... 128/2 F |
| 4,160,646 | 7/1979 | Furutani et al. ........... 436/169 |
| 4,178,153 | 12/1979 | Sodickson .................. 23/230 R |
| 4,661,706 | 4/1987 | Messerschmidt et al. .... 356/446 |
| 4,747,684 | 5/1988 | Weiser ....................... 356/446 |
| 4,770,536 | 9/1988 | Golberstein ............... 356/446 |
| 4,806,764 | 2/1989 | Satake ....................... 250/339.12 |
| 4,823,009 | 4/1989 | Biemann et al. ........... 250/341 |
| 4,889,427 | 12/1989 | Van Veen et al. .......... 356/445 |
| 4,931,384 | 6/1990 | Layton et al. ............. 436/171 |
| 4,960,691 | 10/1990 | Gorden et al. ............. 435/6 |
| 5,019,175 | 5/1991 | Sting et al. ................ 356/445 |
| 5,118,608 | 6/1992 | Layton et al. ............. 436/171 |
| 5,120,643 | 6/1992 | Ching et al. ............... 435/7.92 |
| 5,143,627 | 9/1992 | Lapidus et al. ............ 210/767 |
| 5,334,837 | 8/1994 | Ikeda et al. ............... 250/339 |
| 5,336,599 | 8/1994 | Kitajima .................... 436/170 |
| 5,347,364 | 9/1994 | Kawasaki et al. .......... 356/445 |

FOREIGN PATENT DOCUMENTS

| | | |
|---|---|---|
| 0434800B1 | 6/1990 | European Pat. Off. . |
| 4233231A1 | 4/1993 | Germany . |
| WO90/15981 | 12/1990 | WIPO . |

OTHER PUBLICATIONS

International Publication No. WO 90/15981 filed Dec. 27, 1990.
BAIN et al, *J. Am. Chem. Soc.*, "Formation of Monolayer Films by the Spontaneous Assemply of Organic Thiols from Solution onto Gold", 1989, 111, 321–335.
Prime et al, *Science*, "Self–Assembled Organic Monolayers: Model Systems for Studying Adsorption of Proteins at Surfaces", 252, pp. 1164–1167.

*Primary Examiner*—Jill Warden
*Assistant Examiner*—Sharidan Carrillo
*Attorney, Agent, or Firm*—Nikaido, Marmelstein, Murray & Oram LLP

[57] ABSTRACT

The invention concerns a method for the quantitative analysis of sample liquids. A sample is dried and irradiated with visible and/or infrared light. Light that is diffusely or specularly reflected from the sample and sample carrier is detected and analysed. Furthermore the invention concerns a system for carrying out the method according to the invention and a sample carrier having a diffusely or specularly reflecting surface.

28 Claims, 9 Drawing Sheets

METHOD FOR THE QUANTITATIVE ANALYSIS OF SAMPLE LIQUID

BACKGROUND OF THE INVENTION

1. Field of the Invention

The invention concerns a method for the quantitative analysis of sample liquids by irradiating a sample that has been essentially freed of solvent and detecting the radiation that is diffusely reflected from the sample and sample carrier. In addition the invention includes a system for the analysis of sample liquids with which samples that have been essentially freed of solvent that are located on a sample carrier are irradiated and the radiation emitted from the sample is detected with a detection device. The invention additionally encompasses a sample carrier for use in a system according to the invention in which a diffusely reflecting metal layer is present on a carrier.

2. Description of the Prior Art

Methods for the qualitative analysis of sample liquids are known in the state of the an in which solids, thin layer chromatograms or residues of drying are illuminated with infrared radiation and the reflected radiation is analysed in order to obtain information on substances in the sample. In the disclosure DE-A-42 33 321 a microanalytical method is described in which the sample liquid is applied onto a plastic carrier and subsequently dried up. Measures are described in this disclosure which are aimed to achieve a layer thickness that is as large as possible and as flat a structure as possible of the residue of drying. Only pan of the residue of drying is irradiated with infrared radiation using the described system and the specularly reflected radiation is analysed. Since the radiation passes through only pan of the residue of drying a quantitative analysis is only possible when exactly defined dimensions of the residue of drying can be guaranteed which in practice is very time-consuming.

SUMMARY OF THE INVENTION

In addition methods for the analysis of liquids are described in the state of the an in which for example fruit juices are applied to a glass fibre fleece and analysed by detection of reflected infrared radiation. In this case the radiation only penetrates the upper layer of the fleece. The method has to be empirically calibrated for a quantitative evaluation and is susceptible to error since a variable microstructure of the glass fibre fleece causes interference. Also in the case of the analysis of thin layer chromatograms with scanners, the radiation penetrates a not exactly defined pan of the sample and therefore necessitates an empirical calibration.

The Patent Application WO 90/15981 concerns the drying of filter materials onto which sample liquids have been applied. The drying process represents a central problem in this application because an uncontrolled migration of sample constituents occurs during the drying which has an adverse effect on the homogeneity of the residue of drying. In the analytical method described in WO 90/15981 the radiation penetrates only pan of the sample and is thus less suitable for a quantitative trace analysis.

The state of the an has the disadvantage that a quantitative analysis of sample liquids by measurement of the IR radiation reflected from the sample is only possible when complicated measures are carried out during the sample preparation. In particular it is not possible using the methods known in the state of the an to adequately carry out quantitative analyses when mixtures of substances are present.

The object of the invention was to provide a method and a system for the quantitative analysis of dried up sample liquids which does not have the disadvantages of known methods. In particular the sample preparation should not be critical for the analytical result and not require any complicated measures. The accuracy of known methods should be increased for small sample volumes. In addition it was an object of the invention to enable the quantitative analysis of several analytes simultaneously.

A method for the quantitative analysis of sample liquids was found which comprises the steps applying a defined amount of sample liquid onto the surface of a sample carrier, drying the sample liquid to achieve a residue of drying whose solvent content is below 20% by weight, irradiating the residue of drying with a cone of rays of radiation from the infrared and/or visible range of the spectrum in such a manner that the residue of drying is located completely in the cone of rays, detecting radiation which has been diffusely reflected from the residue of drying and sample carrier, analysing the detected irradiation to calculate the concentration of one or several constituents of the sample liquid.

In addition the invention concerns a system for carrying out a method according to the invention and a sample career which is suitable for use in the system according to the invention.

In the method according to the invention a small amount of sample is applied onto the surface of a sample carrier and subsequently dried. The application of the sample liquid can be carried out with a micropipette. Sample quantities below 50 µl and in particular between 0.1 and 10 µl are preferably used. Since the entire residue of drying of the sample liquid is analysed, the method optimally utilizes the sample quantity.

Sample quantities below 1 µl can only be pipetted with difficulty with an adequately good precision. This applies particularly to sample material such as human serum whose surface tension (40–70 dyne/cm) and viscosity (1.2–1.9 cP) varies within wide ranges. A pipetting procedure has proven to be advantageous for applying the sample onto the sample carrier in which a relatively large amount of sample of for example 10 µl is applied and after the liquid has spread a large proportion e.g. 9.5 µl is removed by suction. Preferably, the amount of sample removed is greater the 50%. In this case the dosing needle must be in direct contact with the carrier surface so that air which would falsify the result, is not sucked up laterally. The suction can be carded out with the same pipetting needle with which the liquid has been applied.

The described pipetting procedure enables very small amounts to be exactly dosed and, moreover, produces a relatively extensive, flat sample spot which is favourable for an analytical method according to the invention.

In a further embodiment of the dosing procedure, a quantity of sample is applied and, after waiting for a time period of several seconds up to one minute, a large part of the sample is removed by suction. This procedure offers the advantage that during the waiting period the sample already starts to dry at the edges of the applied drop. During the drying of the liquid residue remaining after suction, a structure of the residue of drying forms which is particularly favourable for an analysis.

Another method of producing small sample volumes is to specifically drain off the excess of applied sample liquid from the site of measurement. This can for example be accomplished by integrating depressions in the sample carrier which take up liquid by capillary forces. The amount of sample liquid remaining at the site of measurement is determined by the total sample volume minus the volume of the depression.

A transfer print method is also suitable for dosing small sample volumes that are necessary for a method according to the invention. In this method a stamp is wetted with sample liquid and the stamp is pressed onto the sample carrier with a regulated pressure. After the stamp has been lifted from the sample carrier, a quantity of sample remains on the carrier which is dependent on the material of the stamp, the applied pressure, the sample liquid and the carrier material. In particular the material of the stamp and the applied pressure on the sample carrier can be calibrated by experiments in such a way that the applied quantity of sample becomes a defined value.

Materials that come into particular consideration for the stamp are cotton-wool swabs, pads coated with felt or foam rubber and other materials which have an adequate absorptive capacity for liquids.

Liquids that are suitable as sample liquids within the scope of the invention are those which leave a solid residue after drying. These can for example be water samples, fractions of separation processes, foods and natural products. The method according to the invention can be used particularly advantageously in the field of clinical diagnostics e.g. of blood, plasma, haemolysate, serum, urine, saliva or tear fluid. Analytes that can be analysed with the method according to the invention are in particular organic molecules such as glucose, proteins, hormones, glycerides, lipids, enzymes, pharmaceutical agents, drugs and also electrolytes.

The sample liquid can be dried passively i.e. as an evaporation of the solvent or solvents or be actively controlled by special devices. Drying can for example be achieved by blowing air, heating, applying a vacuum or microwave radiation.

The drying of the samples can also advantageously take place while the sample carrier is vibrated. In this manner it is possible to favourably influence the height profile of the residue of drying. A further possibility of favourably influencing the shape of the residue of drying is to add auxiliary substances to the sample. Surface-active substances such as detergents and also proteins have in particular proven to be advantageous. The addition of proteins or other macromolecular substances which suppress formation of crystals is especially recommended when sample liquids are analysed that contain salts which is for example the case for urine. A homogeneous and coherent residue of drying can be achieved by addition of the said auxiliary substances.

The solvent present in the sample liquid can be a single substance as well as a mixture of different substances. Solvents that for example come into consideration are water and organic and inorganic solvents known in the state of the art. Solvents with in the meaning of the invention are generally to be understood as those low molecular substances which can dissolve other substances. The term solvent is not limited to substances that are added in order to achieve a dissolution but rather also encompasses those substances which, when the samples occur naturally, adopt the function of a solvent.

An advantageous aspect of a method according to the invention is the extensive removal of the solvent since in this manner interfering absorptions of radiation that would otherwise cover up absorptions of analytes are eliminated to a large extent.

According to the invention the sample liquid is not completely dried up but only partially. A residual content of solvent of ca. 1% to 20% has mined out to be advantageous. When the drying is complete amorphous powders are formed which hinder a reproducible spectroscopic examination.

The form of the residue of drying obtained by one of the said drying methods can vary within wide limits in a method according to the invention without interfering with a quantitative analysis. Accordingly special measures such as e.g. pressing the residue of drying in order to achieve a smooth surface or pressing into a mould is not necessary. This is important in as much as the form of the residue of drying is considerably dependent on the drying method and the type of sample liquid and can hence only be partially regulated. However, it can be advantageous according to the invention to dry the sample liquid in depressions in order to limit a spreading of the liquid or to use drying methods that favour a particular form of the residue of drying.

A central aspect of the invention is the surface of the sample carrier on which the sample liquid is applied for drying. The surface according to the invention is made in such a way that the sample liquid cannot essentially penetrate into it. However, since every real surface has a certain porosity, there is always a slight penetration of liquid into the surface. According to the invention surfaces are used which, due to their low porosity, only withdraw a very small amount of sample liquid (e.g. less than 1%) from irradiation by the measuring beam.

The said surfaces can for example be metal or metallized plastic surfaces. In the first variant the surface is made in such a way that it diffusely reflects the measuring radiation. Such surfaces can be obtained by treating the surface of metals such as e.g. aluminium, silver, platinum, gold or alloys such as e.g. brass in such a way that they are microscopically plane but have an average depth of roughness of ca. 0.5 to 200 μm. Such depths of roughness can for example be achieved by sand blasting the respective surface with sand of a suitable grain size or by toughening a surface with abrasive materials. Surfaces of sample carriers are preferred according to the invention in which a thin metal layer that reflects well that is made for example of chromium, silver, platinum and in particular gold is coated on a coarse substrate. Since the metal layers are usually very thin because they are deposited by evaporation or sputtered, the carrier material must already have a roughness that ensures a diffuse reflection of the measuring radiation. Preferred average depths of roughness are in the range of 0.5 to 50 μm.

It has turned out according to the invention that average depths of roughness of below 0.5 μm can also be advantageous. The reason for this is that the number of scattering centres is higher which leads to an increase in the intensity of the reflected radiation. For a given analytical problem, the depth of roughness of the surface, detection angle (with respect to the normal of the surface) of reflected radiation and intensity of beamed radiation can be matched in such a way that the sensitivity and accuracy of the measurement are optimal.

Moreover it has also turned out that a method according to the invention can be carried out with specularly reflected radiation. For this embodiment of the invention, surfaces-like the ones already described-are used but their average depth of roughness is so small that no significant scattering occurs. Metal coatings of gold, silver, platinum or brass are particularly suitable.

In an analytical method in which specularly reflected radiation is analysed, radiation is beamed below an angle of 5° to 85° to the surface normal and the radiation reflected at the same angle of reflection is detected. It is also important in this embodiment of the invention that the sample spot on the carrier surface is completely covered by incident radiation in order to enable an integral measurement. The other method steps in this embodiment using reflecting surfaces correspond to those of the measurement using diffuse reflection. The invention therefore also includes the following method:

Method for the quantitative analysis of sample liquid comprising the steps applying a defined amount of sample liquid onto the surface of a sample carrier, drying the sample liquid to achieve a residue of drying whose solvent content is below 20% by weight, irradiating the residue of drying with a cone of rays of radiation from the infrared and/or visible range of the spectrum in such a way that the residue of drying is situated completely within the cone of rays, detecting radiation which has been specularly reflected from the residue of drying and sample carrier, analysing the detected radiation in order to calculate the concentration of one or several constituents of the sample liquid.

The carrier material can in turn be composed of one of the said metals or alloys or be manufactured from a plastic such as polyethylene, polypropylene, polymethacrylate, polycarbonate, polystyrene. Sample carriers or carrier materials that are pressed or casted can be provided directly with a suitable surface roughness during the manufacturing process.

In a further embodiment according to the invention the sample carrier is made in such a way it is at least partially permeable to the radiation used. For this application $CaF_2$, ZnSe, polyethylene and perfluorinated polyethylene come for example into consideration for the infrared range. For measurements in the visible range of the spectrum, materials such as glasses, polystyrene and polyacrylate come into consideration. The underside of the carrier that is permeable to radiation is diffusely or specularly reflecting which can be achieved by a metallization with the aforementioned materials. This embodiment of a sample carrier can be used in particular for reagent coatings since the reflecting layer and the reagent layer can be located on opposite sides of the carrier and hence the reflective layer does not come into direct contact with corrosive reagents.

Radiation frequencies in the range of 300 nm to 25 μm, preferably of 2.5 to 25 μm can be used to carry out a method according to the invention. The radiation range denoted infrared is intended to include the near infrared range. The generation and focussing of the said types of radiation is adequately described in the state of the art. Radiation sources with a continuous spectrum can be used. However, within the scope of the invention it is decisive that the focussing of the beam of rays is matched to the size of the residue of drying. The size of the residue of drying on the surface of the sample carrier depends on the type of sample liquid and the nature of the surface. According to the invention the residue of drying is completely within the irradiated beam of radiation during the measurement. This enables an integral measurement.

An integral measurement is understood as the fact that the entire residue of drying is irradiated and at least part of the radiation reflected or scattered from the residue of drying or from the carrier is detected at a spatial angle determined by the measuring arrangement. The integral measurement in combination with diffusely or specularly reflecting surfaces enables a quantitative analysis of the measurement.

Detectors known in the state of the art for the frequency range used are suitable for detecting the radiation. Semiconductor detectors that can be cooled with liquid nitrogen or Peltier elements are for example suitable. Mercury-cadmium-telluride detectors can be preferably used or those with deuterated triglycine sulfate. According to the invention radiation from the entire residue of drying is passed onto the detector; if desired, focussing devices such as e.g. parabolic mirrors or converging lenses can be placed in between. Infrared microscopes can also be used in which case, however, a collecting device usually has to be placed in front in order to capture radiation diffusely or specularly reflected from the residue of drying and carrier. It is adequate according to the invention when only part of the radiation emitted from the residue of drying is captured, but it must consist of representative contributions from the entire residue of drying.

The generation and detection of the radiation can be achieved with classical grating or prismatic spectrometers; however, the Fourier-transform spectrometers known in the state of the art are preferred.

In the method according to the invention a thin layer of analytical sample that has been substantially freed of solvent is present on a surface. The small layer thickness of the sample ensures that the measuring beam used can penetrate all layers of the sample which is of decisive importance for a quantitative evaluation of the measurement. In the arrangement according to the invention the measuring beam is scattered several times within the sample before it is deflected onto the reflecting surface of the sample carrier and from there arrives at the detector possibly after further multiple scattering in the sample. This leads to an increase in the signal yield in comparison to a transmission arrangement since the effective light path is increased within the sample. Roughening the reflecting sample surface additionally increases the yield of diffuse radiation.

A further increase in the sensitivity of measurement is due to the fact that the sample has been substantially freed of solvent. In this way interfering radiation absorptions by the solvent(s) is reduced. An additional effect is that the components in the residue of drying are concentrated due to evaporation of the solvent(s) which also leads to an increase in sensitivity.

A multicomponent analysis can be achieved by analysing the spectra obtained using chemometric methods. Chemometric methods are known in the state of the art which can be used to carry out a multicomponent analysis such as e.g. partial-least-squares (PLS), principle component regression (PCR) and (NN). A description of possible evaluation methods for determining one or several analytes in a mixture of substances was given for example by D. Haaland in SPIE vol. 1575, 8th International Conference on Fourier Transform Spectroscopy (1991) pages 87–95. An advantage of the method according to the invention is that when using chemometric methods two or several analytes can be detected in simultaneously.

The invention also encompasses a system for the quantitative analysis of sample liquids which comprises a source of radiation whose radiation is in the range of 300 nm to 25 μm, a sample carrier which in at least partial regions diffusely reflects radiation, a dosing device for applying sample liquid to the sample carrier, a detection device for radiation emitted from the sample and an evaluation device for signals of the detection device and is characterized in that the dosing of the sample liquid, the sample carrier and the focussing are matched in such a way that the sample is completely covered by radiation from the radiation source.

In a system according to the invention focussing and dosing are matched. A focussing of radiation in the infrared or visible range can be achieved with lens systems and diaphragms wherein lenses made of $CaF_2$, KCl, KBr and other materials have to be used in the infrared range which have an adequate permeability for the spectral range to be measured.

The important requirement for the invention, i.e. that the sample is located completely within the cone of rays of the radiation source, can also be achieved by appropriately limiting the size of the sample. This can be achieved by only applying a small amount of sample liquid which occupies an area on the surface of the test carrier that is smaller than the cone of rays impinging on the test carrier. The area occupied by the applied liquid is on the one hand dependent on the type of liquid and in particular on its viscosity and surface tension and on the other hand on the nature of the surface. Accordingly the surface can be treated in order to change its quality. The surface of the test carrier can be mechanically modified so that it has depressions into which the sample liquid is applied. The depressions can for example have edges that are formed perpendicularly to the surface of the test carrier or have sloping edges. It is also possible to have depressions in the form of spherical segments or paraboloid segments.

In a particularly preferred embodiment of the sample carrier this has a smooth surface which is roughened at selected sites. Th roughened zones preferably have a circular shape and are somewhat smaller than the cone of radiation of the measuring beam. This embodiment of the sample carrier offers the advantage that the spreading of the sample liquid is limited to the roughened zones. It is therefore possible to apply a relatively large sample volume onto a small surface zone which leads to a high concentration of the substances to be examined in the cone of radiation. In a preferred embodiment of the sample carrier the roughened zones have a diameter of 1 to 20 mm.

The spreading of the sample liquid on the carrier can also be achieved by a suitable surface coating of the carrier. Zones which are intended for receiving the sample liquid can be coated hydrophilically. Equally it is possible to limit spreading of the sample with a hydrophobic coating around the sample application zones. For example a Teflon mask can be sprayed on, which represents a hydrophobic barrier to aqueous sample liquids.

Alkyl chains with terminal thiol groups are suitable for coating gold surfaces since the thiol group binds well to gold surfaces. For a hydrophilic coating, the alkyl chains for example carry sulfonic acid groups, phosphate residues or carboxyl groups. Longer alkyl chains or alkyl chains with organic residues are preferably used for a hydrophobic coating. The formation of surface coatings and suitable substances are described e.g. in J. Am. Chem. Soc. 1989, vol. 111, pages 321–335 as well as in Science, vol. 252, pages 1164–1167.

A further method of binding the alkyl chains which may be substituted to surfaces is to use photoreactions in which reactive intermediates are released which bind directly to the metal surfaces.

In practice it will not be possible to prevent the detected signal from containing information on the surface of the carrier since the cone of radiation completely covers the residue of drying and usually also irradiates adjoining positions on the surface of the sample carrier. Materials can be selected for the sample carrier and in particular for its surface which do not cause any interference in spectral regions that are important for the analysis. If the said materials have a constant absorption in the frequency range of the measurement then this can be substracted from the measured spectrum. In particular the described surface coatings do not represent a significant interfering signal since the applied coats are monomolecular and thus their contribution to the measured signal is negligible.

The invention in addition concerns a sample carrier in which a reflecting layer is applied to at least one surface of a carrier wherein the resulting at least one surface is characterized in that it has a depth of roughness of less than 200 µm, preferably of 0.5 to 50 µm.

It is important according to the invention that the surfaces on which the sample liquid is applied diffusely reflect light. Depths of roughness according to the invention can be produced by treating the surface with abrasive materials, sand blasting, etching etc. As described above the sample carrier can be composed of a carrier material and a reflecting layer applied thereon.

In a further variant reagents are located on the sample carrier that react in a characteristic manner with the analytes to be detected. These reagents are preferably located in depressions of the sample carrier. It is particularly important that it is possible to carry out the analysis with addition of reagents for enzymes, electrolytes, hormones, proteins and other analytes that only occur in very small concentrations. In the case of enzymes the enzymatic activity can for example be utilized in order to release dyes which are in turn detected.

A method according to the invention is also suitable for the determination of the kinetics of reactions in particular of enzymatic reactions. This can for example be carried out with coated sample carriers on the surface of which the reagents or enzymes are located. When the sample liquid is applied the reagents or enzymes are dissolved and react with components of the sample. In order to determine the kinetics repeated measurements are carried out at intervals according to methods according to the invention and from this the kinetics of the reaction to be examined are determined. It has turned out that a determination of the reaction kinetics is also possible when the sample liquid has been partially dried on the carrier.

When reagents are used on the sample carrier, then such embodiments of the sample carrier are preferred in which the reagents are located on an inert carrier layer. If for example plastics are used as the carrier materials then the metallization of the sample carrier is preferably located on the side opposite to the reagent in order to prevent corrosion of the metallization by action of the reagents.

In addition to the already described sample carriers into which the sample liquid cannot penetrate or only to an insubstantial extent, those sample carriers can also be used according to the invention which have an absorbent layer into which the sample liquid penetrates. It is important for a quantitative evaluation that the amount of sample covered by the cone of radiation assumes a clearly defined value. This can then be achieved in the case of absorbent layers when the depth of penetration of the measuring beam into the absorbent layer is reproducible and the sample volume in the region covered by the measuring beam is also reproducible. In the field of test strips for e.g. blood glucose absorbent layers are known which take up a defined amount of liquid when the sample liquid is applied and pass on excess liquid to adjacent absorbent layers. An arrangement is for example possible in which a multilayer test strip is used whose upper layer can take up a defined amount of liquid, under this layer an optical barrier layer, e.g. of titanium dioxide, is located and a second absorbent layer is placed under this which takes up excess sample liquid. Such an arrangement is for example known from the European Patent specification EP-B-0 434 800.

Using the described arrangement of absorbent layers it is possible to separate small sample volumes from the pipetted quantity. This is advantageous since smaller sample volumes that can only be pipetted with difficulty can also be analysed well using the analytical method according to the invention. Accordingly a suitable arrangement of absorbent layers enables a quantitative analysis.

In a further advantageous embodiment of a ample carrier, this has a sample application zone which is connected to a reservoir for the uptake of liquid. The sample application zone is preferably a depression in the sample carrier that is accessible to radiation which is connected to the reservoir via a channel. In this case it is decisive that the liquid present in the reservoir is not accessible to the radiation. This is for example the case when the reservoir is also a depression on the surface of the carrier which, however, is not covered by the cone of radiation.

The said embodiment of the sample carrier with reservoir is advantageous since it enables a small portion that as such could only be pipetted inaccurately with a pipette to be separated for the analysis from a readily dosable sample volume.

BRIEF DESCRIPTION OF THE DRAWINGS

The following figures are intended to elucidate the invention further.

DETAILED DESCRIPTION OF THE PREFERRED EMBODIMENT

Figure 1:
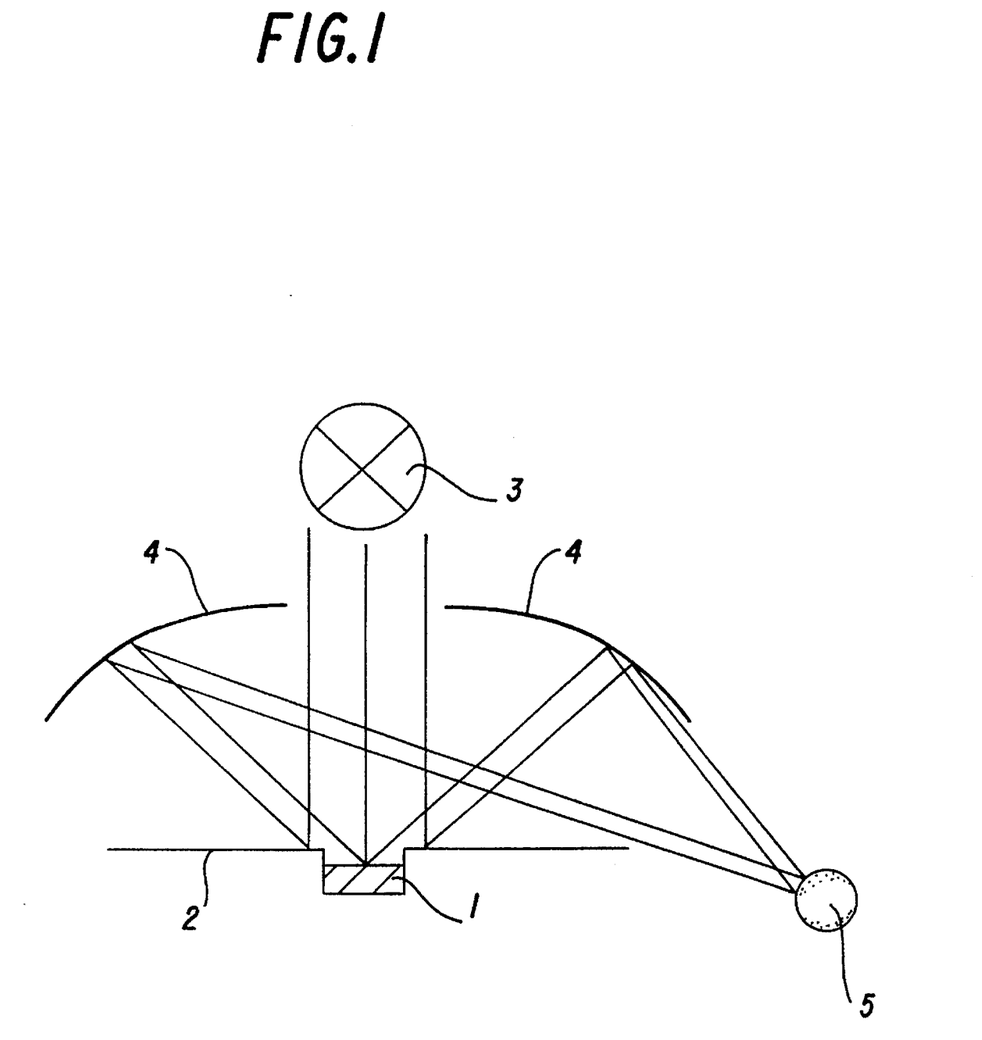
FIG. 1: Arrangement for measuring in diffuse reflection

FIG. 1 shows an arrangement for measuring the diffuse reflection from the residue of drying and sample carrier. The residue of drying (1) is located on a roughened sample carrier (2) whose surface is metallized. The beam of radiation emitted by the radiation source (3) passes through the aperture of the concave mirror (4) onto the residue of drying (1). Radiation is diffusely reflected from this and from the surface and reflected by the concave mirror (4) onto the detector (5). The beam of radiation emitted by the radiation source (3) is so large that it completely covers the residue of drying (1) and also illuminates part of the sample carrier (2).

Figure 2A:
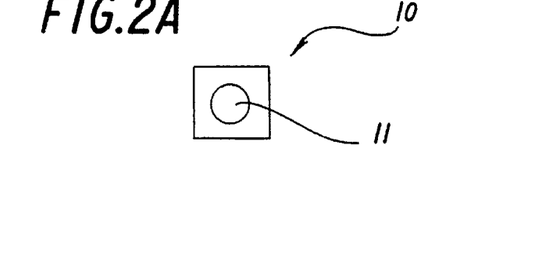
FIG. 2: Sample carrier, simple construction
Figure 2B:
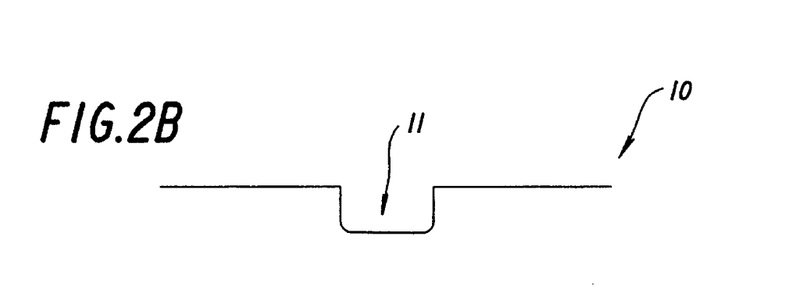

FIGS. 2A and 2B show a sample career (10) which can be used in a system according to the invention. A gold layer of ca. 200 nm thickness is sputtered onto a carrier material made of polystyrene. The depression (11) in the middle of the sample carrier has a diameter of 2.5 mm and a depth of 0.5 mm. The carrier material has an average depth of roughness of ca. 5 µm.

Figure 2C:
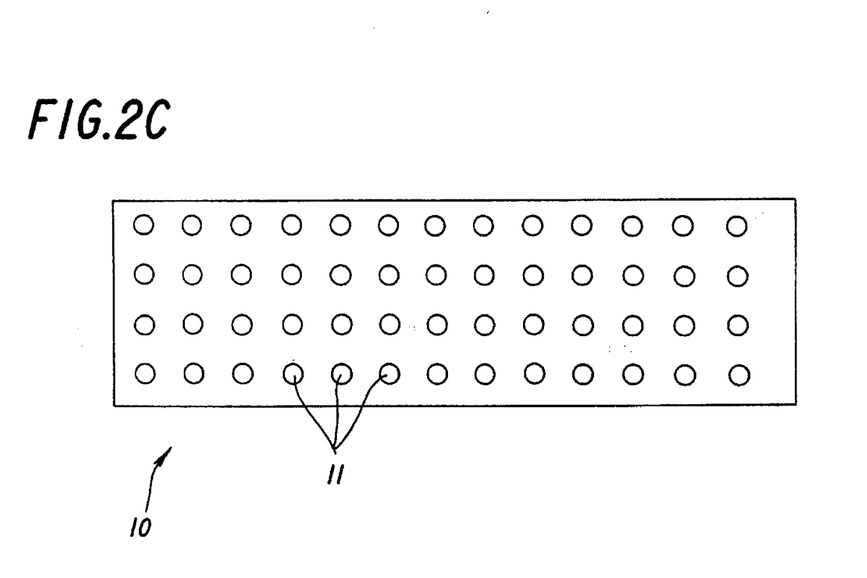

A sample carrier (10) is shown in FIG. 2C which has a plurality of depressions (11). This arrangement is advantageous when it is for example intended to analyse blood samples from several persons or when sample material from one source is to be admixed with different reagents.

Figure 3A:
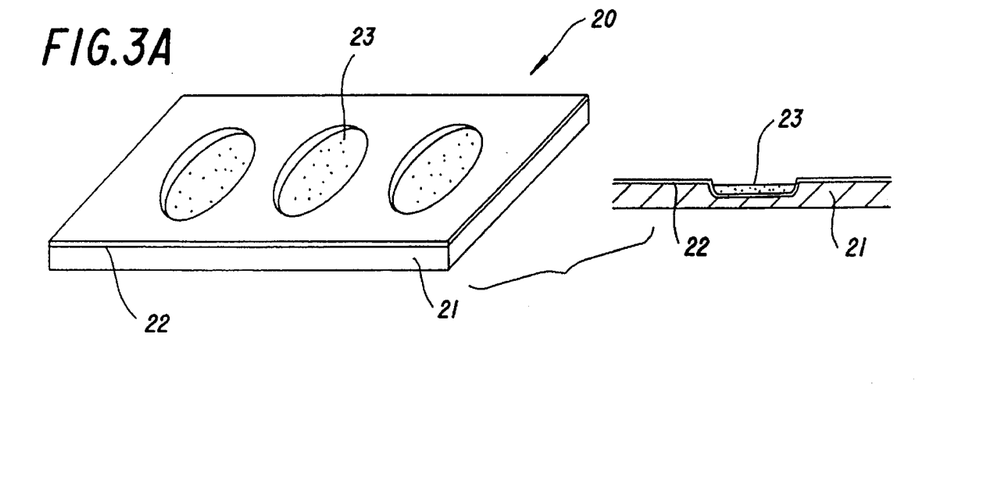
FIG. 3: Sample carrier, extended construction

FIG. 3 shows different embodiments of sample carriers. The sample carrier (20) in FIG. 3A has a carrier layer (21) made of polystyrene on which a metal film (22) made of gold is applied. The depression (23) of the sample carrier is filled with an absorbent layer made of an inert material e.g. titanium dioxide or silica gel. This absorbent layer serves to achieve a uniform spreading of the liquid as well as to amplify the diffuse scattering in the sample. The absorbent layer is so thin that it can be penetrated by the radiation used.

Figure 3B:
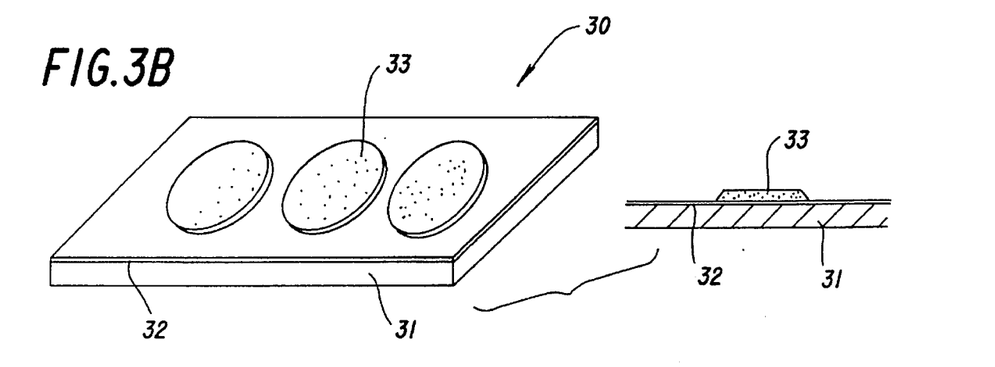

FIG. 3B shows a sample carrier (30) in which a gold film (32) is located on a carrier layer (31) made of polystyrene. A thin absorbent layer made of titanium dioxide is coated as an elevation on the gold film (32). The spreading of the sample liquid is limited to the area of the elevation by the absorbent properties of this layer.

In an embodiment of the invention with reagents on the carrier material these can for example be embedded in the absorbent layer and immobilized therein. When a sample is applied a simultaneous spreading and mixing with reagents then takes place. The reflecting metal layer is preferably located in this case on the side opposite to the absorbent layer of an at least partially transparent carrier.

Figure 3C:
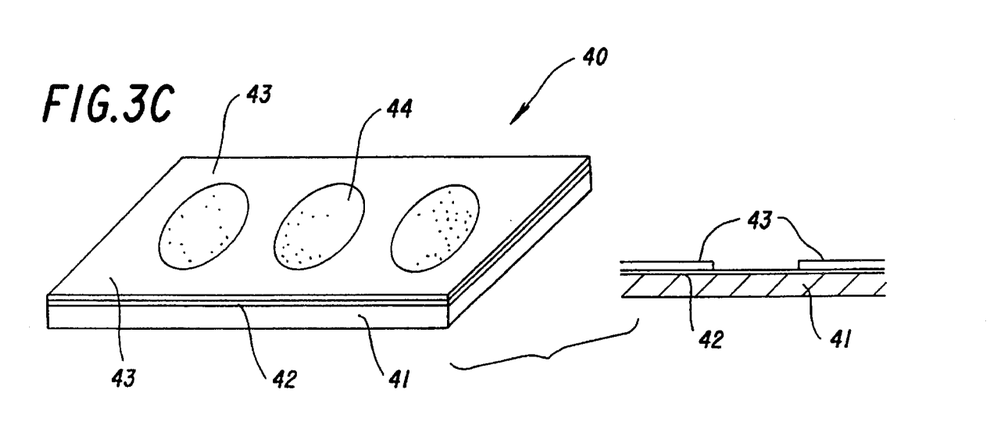

A further embodiment of a sample carrier (40) is shown in FIG. 3C. The carrier layer (41) is again made of polystyrene on which a gold film (42) is applied. A Teflon layer (43) is located on the gold film (42) which has recesses (44) into which the sample liquid can be applied. Since Teflon has strong hydrophobic properties, a hydrophilic sample liquid cannot move beyond a recess (44).

FIG. 7 illustrates an embodiment of the invention wherein a defined amount of sample liquid 50 is placed onto sample carrier 51, as shown in steps a) and b). Step d) illustrates a part 52 of the sample amount 50 being removed, as fully shown in steps c), d) and e).

FIG. 8 illustrates a sample liquid 64 being taken up by absorbent stamp 65. The absorbent stamp is then used to transfer a defined amount 60 from the absorbent stamp 65 onto the surface of sample carrier 61.

List of reference symbols (1) residue of drying
(2) sample carrier
(3) radiation source
(4) concave mirror
(5) detector
(10) sample carrier
(11) depression
(20) sample carrier
(21) carrier layer
(22) metal film
(23) depression
(30) sample carrier
(31) carrier layer
(32) metal film
(33) elevation
(40) sample carrier
(41) carrier layer
(42) metal film (43) hydrophobic layer
(44) recesses The following examples are intended to elucidate the invention in more detail:

Example 1

Glucose determination in serum

5 μl serum was aspirated from a serum sample using a dispenser. 1 μl of this 5 μl was pipetted onto a flat, diffusely reflecting surface of a sample carrier with an average depth of roughness of ca. 5 μm. The material of the sample carrier was gold-plated brass. The sample carrier was allowed to stand at room temperature for ca. ½ hour and as a result the drop dried up. The residue of drying was measured integrally in diffuse reflection using a system according to FIG. 1. The measurement must be carried out in a time window of ca. 30 min up to a maximum of 5 hours since otherwise changes occur in the dried sample which lead to non-reproducible results.

For the example glucose, a region was selected from the spectrum between 950 and 1200 wave numbers on which the PLS method (partial-least-squares) was applied.

Figure 4:
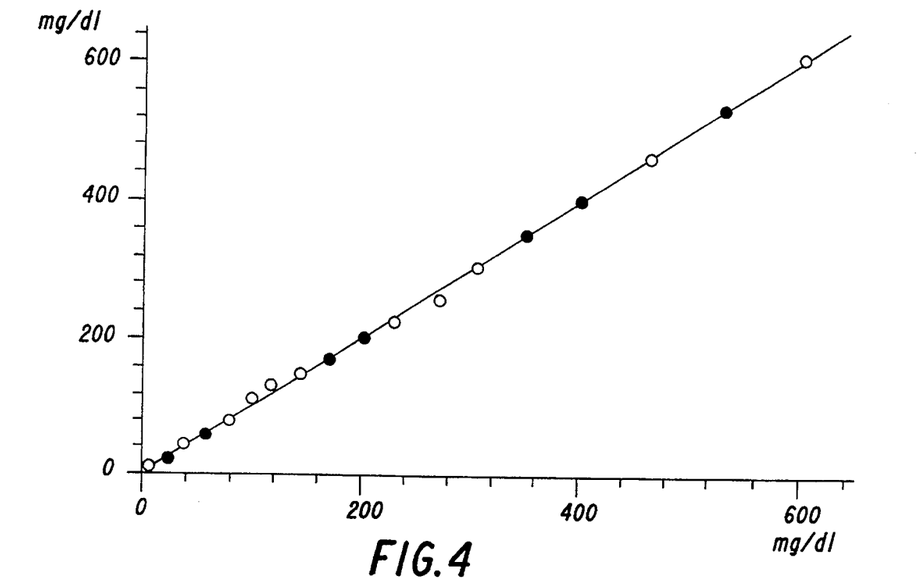
FIG. 4: Method comparison of a glucose determination in human sera.

FIG. 4 shows a method comparison for the determination of glucose. The concentrations in mg/dl of the reference method (hexokinase method) are plotted on the X axis. The prediction model for glucose determined from the IR spectrum by the PLS method is plotted on the Y axis. The black points show the calibration which was used to develop the prediction model. The white points show unknown samples that were not part of the set of calibration data and which were predicted on the basis of the spectrum. The deviations of the white circles from the straight line give an impression of the accuracy of the method.

The accuracy of prediction for unknown samples is comparable with classical enzymatic methods.

Example 2

Triglyceride determination in serum

5 μl serum was aspirated by a dispenser from a random serum sample. 1 μl of this 5 μl was pipetted into a depression of 2.5 mm diameter and a depth of 0.5 mm. The carrier material is gold-plated brass with an average depth of roughness of ca. 5 μm. The sample carrier was allowed to stand at room temperature for ca.

½ hour until the drop dried up. Afterwards the applied serum sample was measured integrally in diffuse reflection using a system according to FIG. 1. The measurement must be carried out in a time window of ca. 30 min up to a maximum of 5 hours. The spectra obtained were analysed in wave number ranges between 2800 and 3080 cm$^{-1}$ as well as 1700 and 1800 cm$^{-1}$ and a prediction model was established from this using the PLS method.

Figure 5:
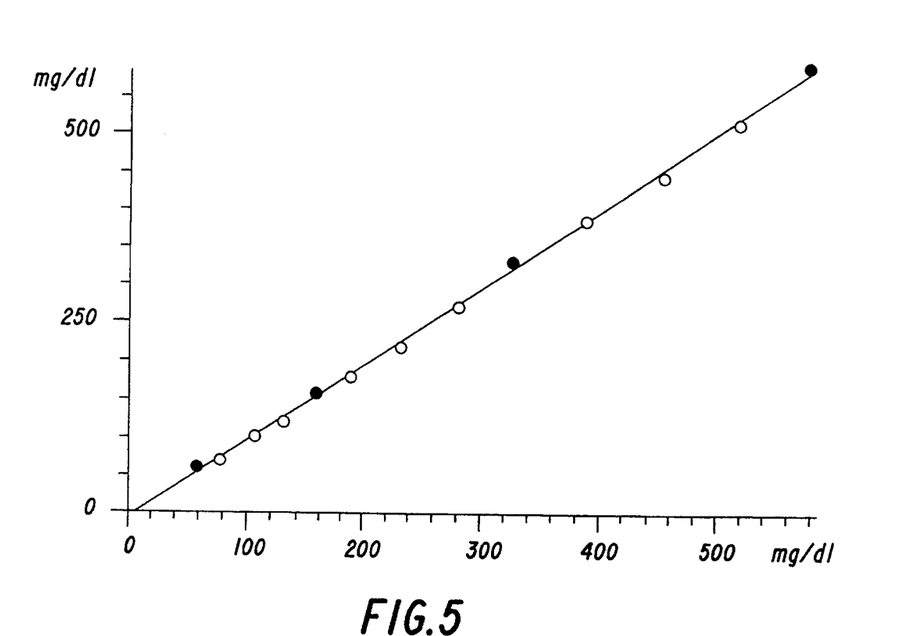
FIG. 5: Method comparison of a triglyceride determination in human sera.

FIG. 5 shows the determination of triglycerides in comparison to the reference measurement on the Hitachi 704 clinical analyzer using the GPO-PAP method. The black points are the calibration samples which were used to develop the prediction model; the white points show unknown samples whose concentrations were obtained for the Y axis on the basis of the prediction model. In this case the precision is also comparable to methods carried out using classical enzymatic methods.

Example 3

Comparison of glucose determinations from capillary blood

Figure 6A:
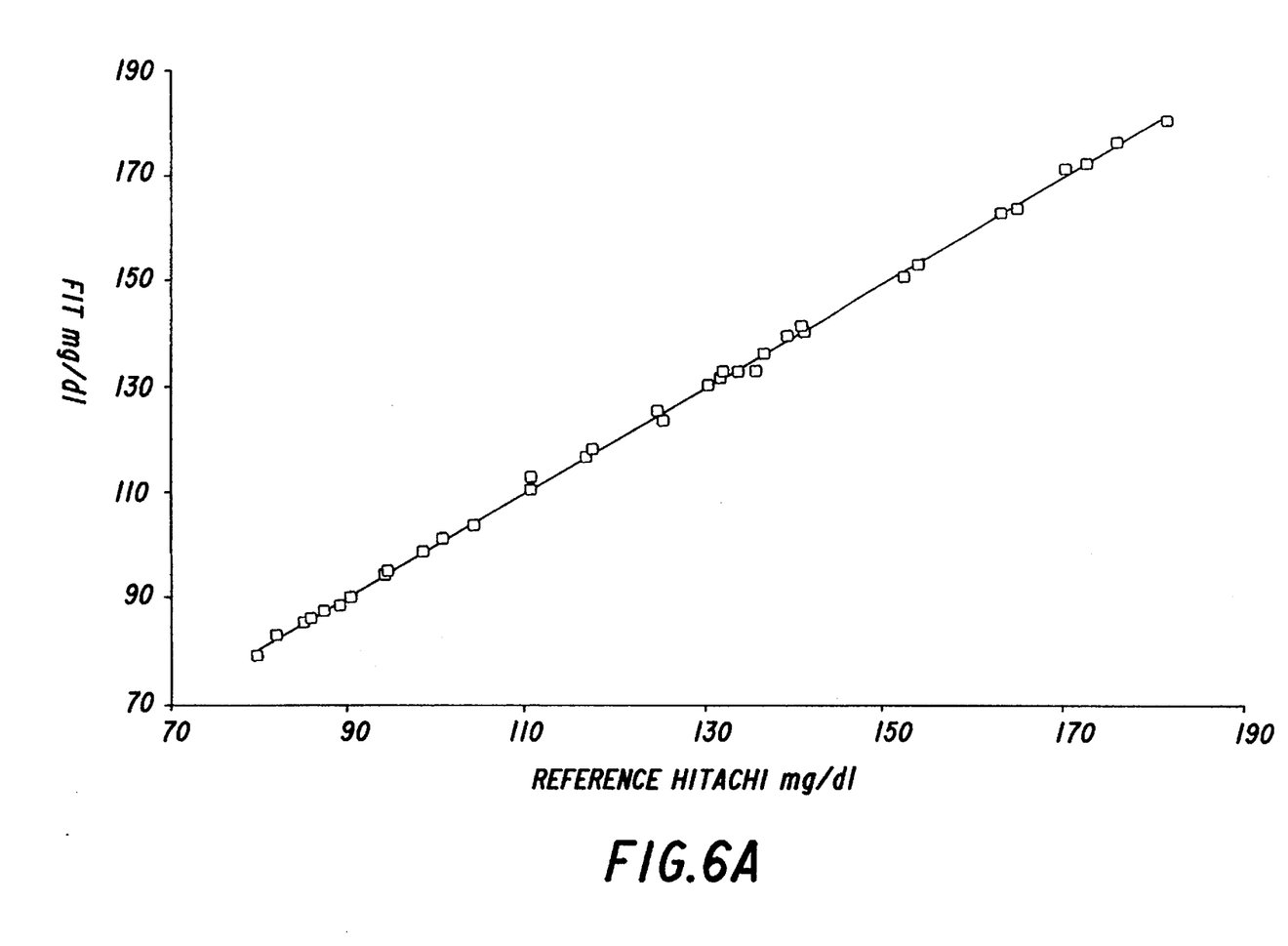
FIG. 6: Method comparison for glucose determinations in capillary blood.
Figure 6B:
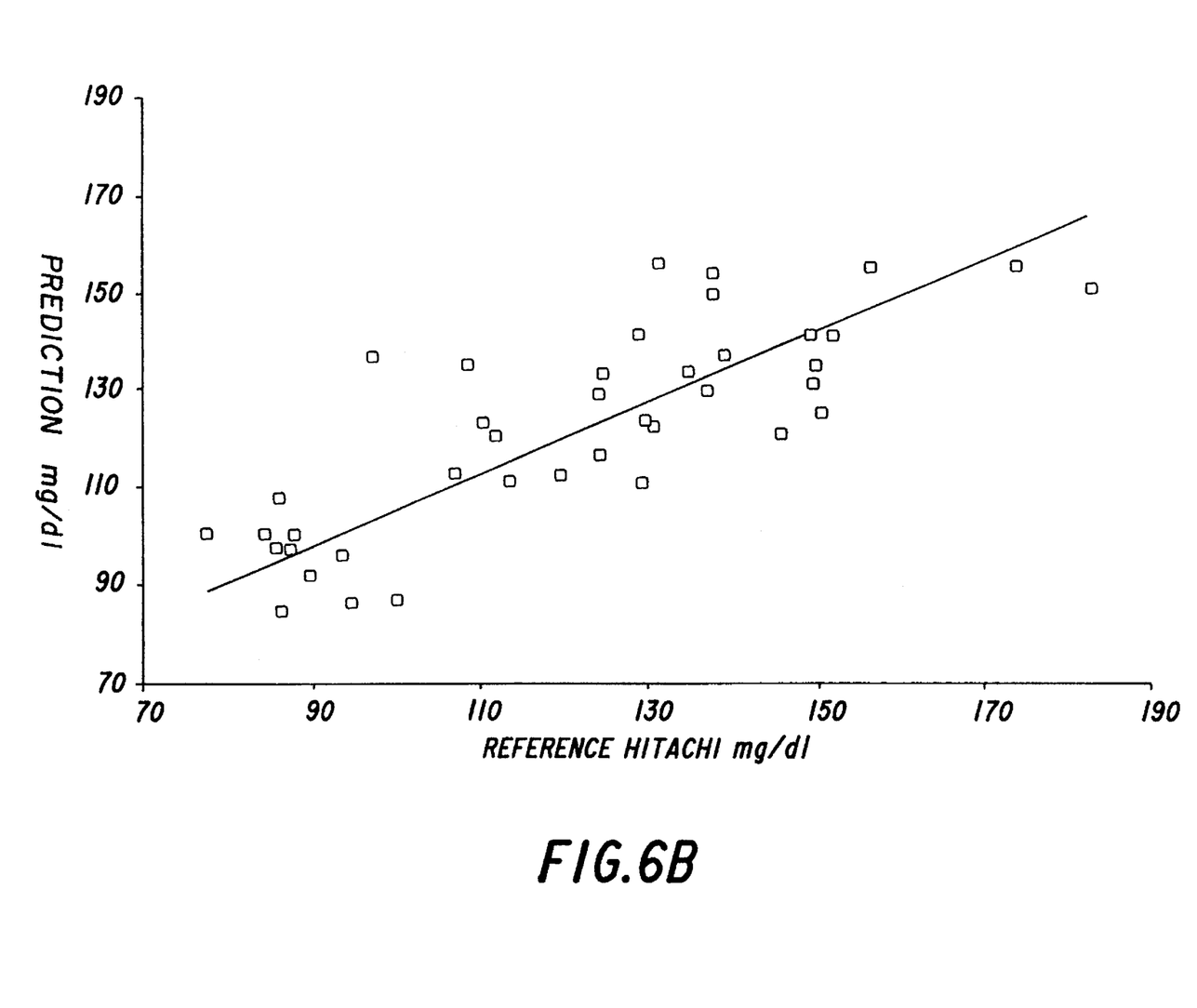
Figure 6C:
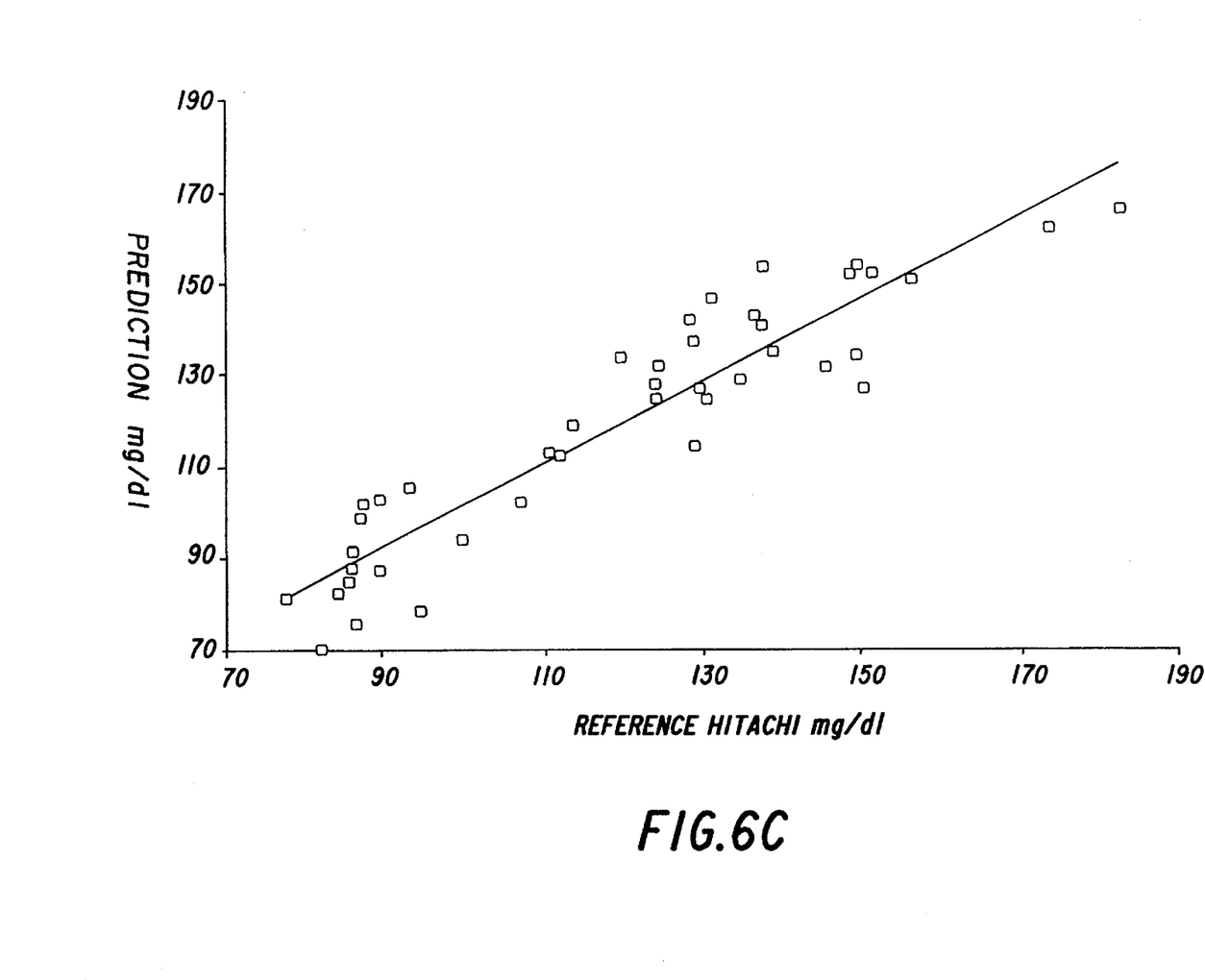
Figure 7A:
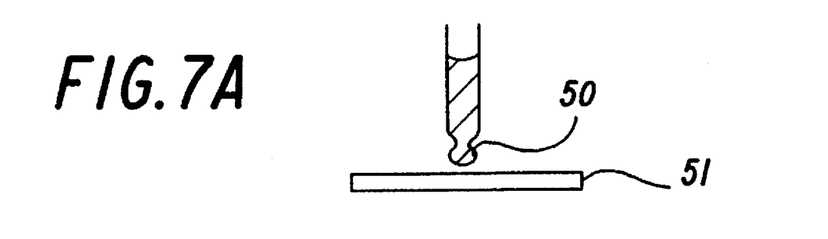
FIG. 7: Method steps a) through e) of applying a sample to and removing a part of a sample from a sample carrier.
Figure 7B:
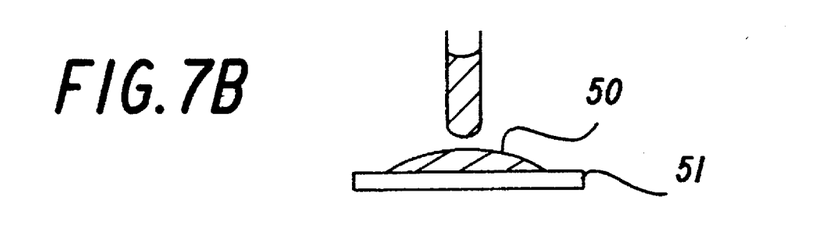
Figure 7C:
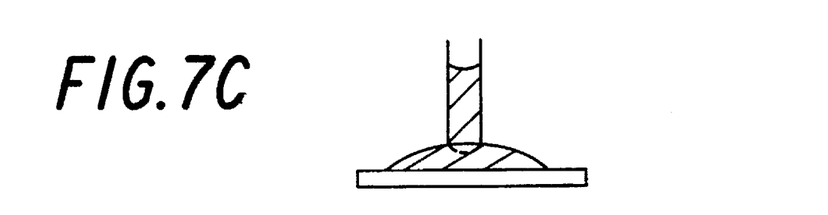
Figure 7D:
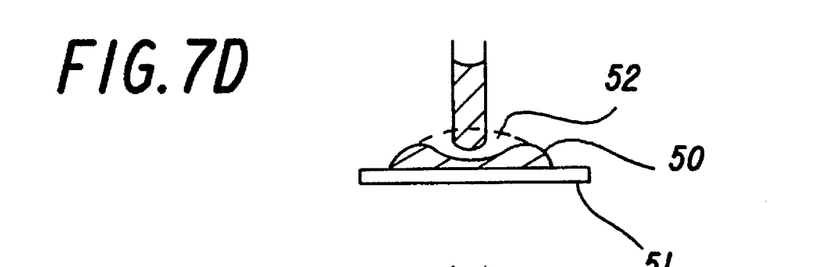
Figure 7E:
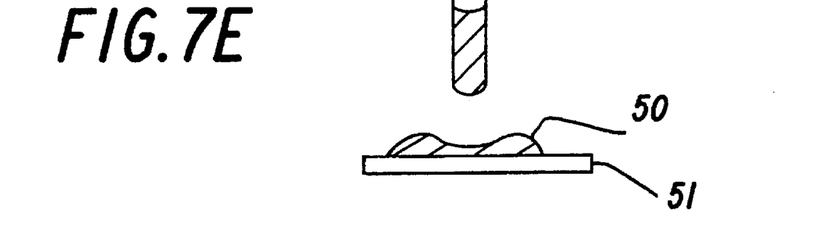
Figure 8A:
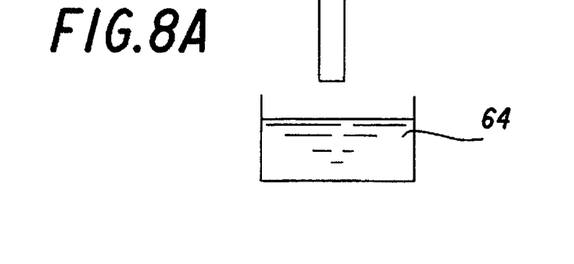
FIG. 8: Method steps a) through e) of applying the sample to a carrier surface utilizing an absorbent stamp.
Figure 8B:
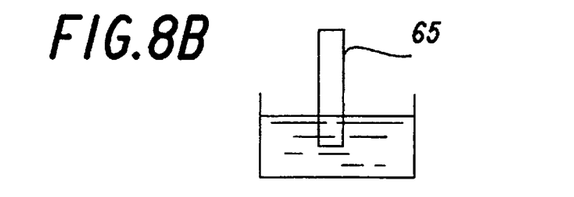
Figure 8C:
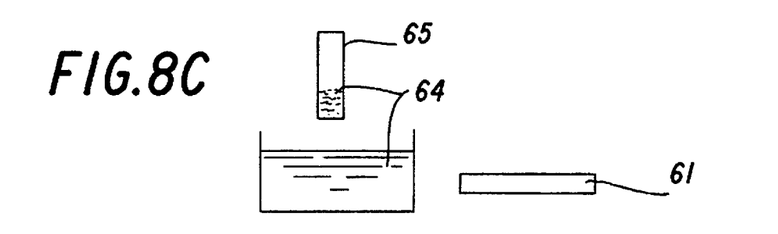
Figure 8D:
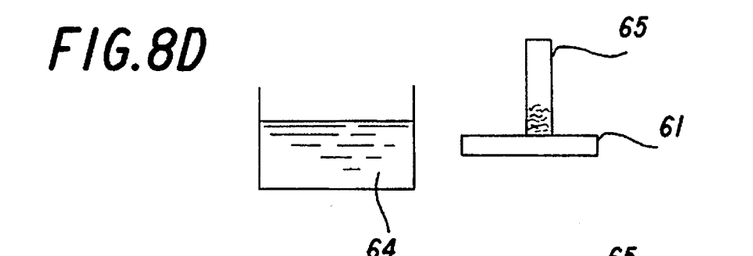
Figure 8E:
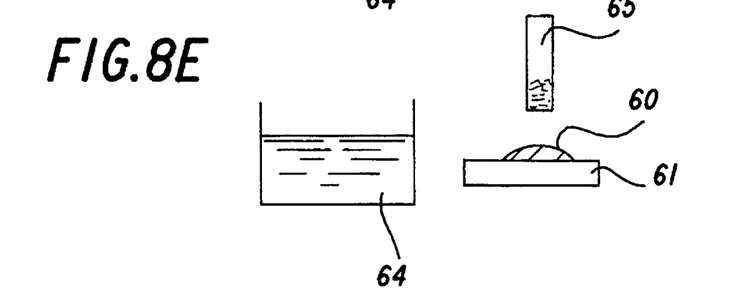

FIGS. 6A, 6B and 6C show a method comparison for glucose determination by the method according to the invention and using the Hitachi 704 analyzer. In the measurements by the method according to the invention, a prepared sample was applied to a gold-coated brass carrier with an average depth of roughness of ca. 0.5–1 μm and the sample was dried under standard room conditions. The wave number range of 960 to 1200 cm$^{-1}$ was selected for the analysis. The analysis was carried out using a multivariate statistic according to the "partial least squares" method.

FIG. 6A shows measurements of capillary blood which were used to calibrate the method according to the invention. The small deviations of the measurement points from the plotted lines show the good agreement between the methods used.

FIG. 6B shows a comparison of the method according to the invention with a reference method for untreated capillary blood. The measurements were carried out on samples with unknown glucose concentration and analysed with the aid of the prediction model from FIG. 6A. A clear correlation can be seen between the method according to the invention and the reference method.

FIG. 6C shows the results of a haemolysate measurement series. A haemolysis can be achieved by adding reagents or in the simplest case by adding distilled water to whole blood. This results in bursting of the cells in the process of which cell constituents are released. The haemolysate is isolated from the treated sample by removing the cell debris for example by centrifugation. The measurements were carried out on haemolysed capillary blood samples of unknown glucose concentration and also show a clear correlation of the methods.

We claim:

1. A method for the quantitative analysis of sample liquids, comprising the steps of:

applying a defined amount of sample liquid containing a solvent and at least one component to be analyzed on the surface of a sample carrier, drying the sample liquid to produce a residue of drying having a solvent content below 20% by weight, irradiating the residue of drying with a cone of rays of radiation in at least one of the infrared or visible range of the spectrum, wherein the residue of drying is located completely in the cone of rays, detecting radiation which has been diffusely reflected from the residue of drying and the sample carrier, and analyzing the detected radiation in order to calculate the concentration of at least one constituent of the sample liquid.

2. Method of claim 1, wherein less than 50 μl of sample liquid is applied to the sample carrier surface in a coherent form.

3. Method of claim 2, wherein the amount of sample liquid is from 0.1 to 10 μl.

4. Method of claim 1, wherein the sample liquid is a body fluid.

5. Method of claim 1, wherein the radiation has wavelengths in the range of 0.3 to 25 μm.

6. Method of claim 5, wherein the radiation wavelengths are in the range of 2.5 to 25 μm.

7. Method of claim 1, wherein the sample liquid cannot penetrate into a substantial portion of the surface of the sample carrier.

8. Method of claim 1, further comprising coating the surface of said sample carrier with reagents suitable for the determination of repeated kinetic measurements.

9. Method of claim 1, wherein the sample liquid is applied to the sample carrier surface by first applying an amount of sample, and thereafter removing a part of the sample amount.

10. Method of claim 9, wherein the part of the sample amount removed is greater than 50%.

11. Method of claim 9, wherein the steps of the application of the liquid sample and the removal of part of the liquid sample are carried out using a pipetting means.

12. Method of claim 1, wherein the sample liquid is applied to the sample carrier surface by taking up the sample on an absorbent stamp, thereafter pressing the stamp onto the surface of the sample carrier and lifting the stamp from the surface to leave the amount of sample liquid on the sample carrier surface.

13. Method of claim 1 wherein detergents, proteins or macromolecular substances are added to the sample liquid in order to change the drying and/or film-forming properties of the sample liquid.

14. A method for the quantitative analysis of sample liquids, comprising the steps of:

applying a defined amount of sample liquid containing a solvent and at least one component to be analyzed on the surface of a sample carrier, drying the sample liquid to produce a residue of drying having a solvent content below 20% by weight, irradiating the residue of drying with a cone of rays of radiation in at least one of the infrared or visible range of the spectrum, wherein the residue of drying is located completely in the cone of rays, detecting radiation which has been specularly reflected from the residue of drying and the sample carrier, and analyzing the detected radiation in order to calculate the concentration of at least one constituent of the sample liquid.

15. Method of claim 14, wherein less than 50 μl of sample liquid is applied to the sample carrier surface in a coherent form.

16. Method of claim 15, wherein the amount of sample liquid is from 0.1 to 10 μl.

17. Method of claim 14, wherein the sample liquid is a body fluid.

18. Method of claim 14, wherein the radiation has wavelengths in the range of 0.3 to 25 μm.

19. Method of claim 18, wherein the radiation wavelengths are in the range of 2.5 to 25 μm.

20. Method of claim 14, wherein the sample liquid cannot penetrate into a substantial portion of the surface of the sample carrier.

21. Method of claim 14, further comprising coating the surface of said sample carrier with reagents suitable for the determination of repeated kinetic measurements.

22. Method of claim 14, wherein the sample liquid is applied to the sample carrier surface by first applying an amount of sample, and thereafter removing a part of the sample amount.

23. Method of claim 22, wherein the part of the sample amount removed is greater than 50%.

24. Method of claim 22, wherein the steps of the application of the liquid sample and the removal of part of the liquid sample are carried out using a pipetting means.

25. Method of claim 14, wherein the sample liquid is applied to the sample carrier surface by taking up the sample on an absorbent stamp, thereafter a pressing the stamp onto the surface of the sample carrier and a lifting the stamp from the surface to leave the amount of sample. liquid on the sample carrier surface.

26. Method of claim 14, wherein detergents, proteins or macromolecular substances are added to the sample liquid in order to change the drying and/or film forming properties of the sample liquid.

27. Method of claim 14, wherein the sample carrier has an average depth of roughness of less than 200 μm.

28. Method of claim 1, wherein the sample carrier has an average depth of roughness of less than 200 μm.

* * * * *